United States Patent
Hadd et al.

(10) Patent No.: US 10,345,211 B2
(45) Date of Patent: Jul. 9, 2019

(54) METHOD OF DETERMINING A CONCENTRATION OF A MATERIAL NOT DISSOLVED BY SILICON ETCHANTS CONTAMINATING A PRODUCT

(71) Applicant: Hemlock Semiconductor Corporation, Hemlock, MI (US)

(72) Inventors: John W. Hadd, Saginaw, MI (US); Robert Scott Leser, Midland, MI (US); Jonathon Host, Midland, MI (US)

(73) Assignee: HEMLOCK SEMICONDUCTOR OPERATIONS LLC, Hemlock, MI (US)

( * ) Notice: Subject to any disclaimer, the term of this patent is extended or adjusted under 35 U.S.C. 154(b) by 429 days.

(21) Appl. No.: 15/082,164

(22) Filed: Mar. 28, 2016

(65) Prior Publication Data
US 2017/0276582 A1 Sep. 28, 2017

(51) Int. Cl.
*G01N 5/04* (2006.01)
*C01B 33/037* (2006.01)

(52) U.S. Cl.
CPC ............. *G01N 5/04* (2013.01); *C01B 33/037* (2013.01)

(58) Field of Classification Search
CPC ................................. G01N 5/04; C01B 33/037
USPC ......................................................... 73/432.1
See application file for complete search history.

(56) References Cited

U.S. PATENT DOCUMENTS

| 6,021,789 A | 2/2000 | Akatsu et al. |
| 6,803,235 B1 | 10/2004 | Mize et al. |
| 2013/0216466 A1 | 8/2013 | Traunspurger et al. |
| 2015/0075559 A1 | 3/2015 | Wochner et al. |

*Primary Examiner* — Jamel E Williams
(74) *Attorney, Agent, or Firm* — Cantor Colburn LLP

(57) ABSTRACT

A method of determining a concentration of plastic or other material not dissolved by silicon etchants contaminating a silicon product comprising: obtaining a sample of the silicon product contaminated with the plastic or other material not dissolved by silicon etchants; placing the sample of the silicon product into a ultrasonic bath liquid to produce a slurry comprising the ultrasonic bath liquid, silicon dust, and the plastic or other material not dissolved by silicon etchants; filtering the slurry with a first filter to produce a cake comprising the silicon dust and the plastic or other material not dissolved by silicon etchants separated from the sample of the silicon product; and analyzing the cake to determine the concentration of plastic or other material not dissolved by silicon etchants contaminating the silicon product.

18 Claims, 1 Drawing Sheet

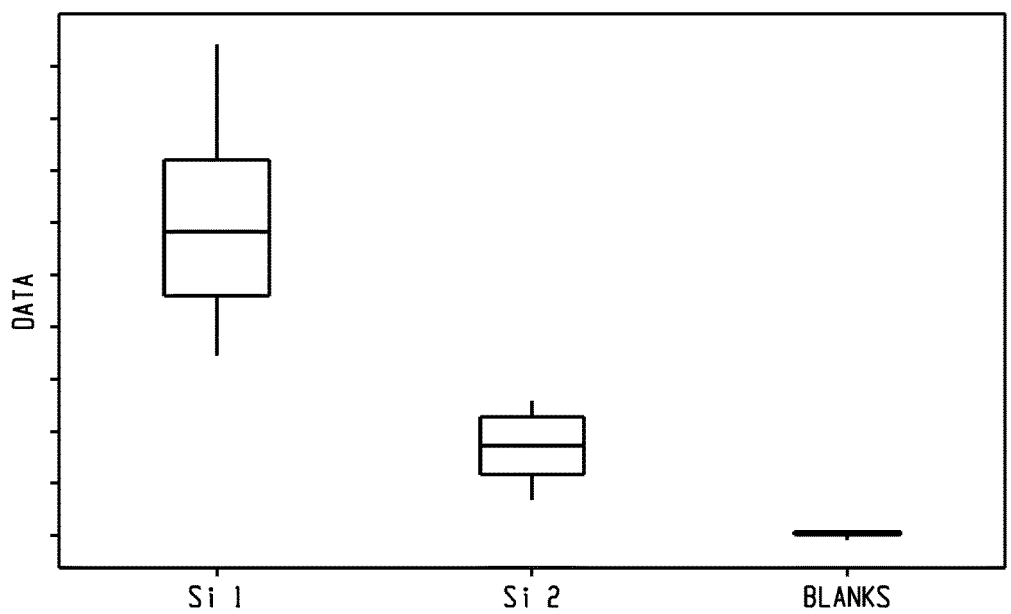

METHOD OF DETERMINING A CONCENTRATION OF A MATERIAL NOT DISSOLVED BY SILICON ETCHANTS CONTAMINATING A PRODUCT

TECHNICAL FIELD

Disclosed herein is a method of determining a concentration of material contaminating a silicon product.

BACKGROUND

Silicon products are used in various applications. In some applications, it is desirable to produce silicon products with a high purity, e.g., purity exceeding metallurgical grade silicon. For example, production of high-density integrated circuits requires wafers of monocrystalline silicon of high purity. Metal impurities on the silicon product, such as copper, gold, iron, cobalt, nickel, chromium, tantalum, zinc, tungsten, titanium, magnesium, molybdenum, and aluminum can be harmful to the production of such integrated circuits.

In an effort to produce silicon products with high purity, contact of the silicon product with other materials is generally avoided to prevent contamination of the silicon product. For example, contact of the silicon product with metal containing materials is avoided to prevent the metal from being transferred to the silicon product thereby contaminating the silicon product. Metal contamination of the silicon product can severely limit the end use of the silicon product. As such, the use of metal containing material in contact with the silicon product is avoided.

To reduce the exposure of the silicon product to metal containing materials, items contacting the silicon product can be made from or coated with plastic materials or other materials not dissolved by silicon etchants. For example, when the silicon product is polycrystalline silicon, hammers made of a plastic material can be used to chunk the polycrystalline silicon for further processing of the polycrystalline silicon. However, contact of the plastic or other material not dissolved by silicon etchants with the silicon product can result in a transfer of the plastic or other material not dissolved by silicon etchants to a surface of the silicon product. The plastic or other material not dissolved by silicon etchants on the surface of the silicon product is a source of carbon contamination, which can limit the end use of the silicon product.

In most cases, the contamination from the plastic or other material not dissolved by silicon etchants on the silicon product is insignificant and does not limit subsequent processing of the silicon product. However, in some applications, such as high performance electronic applications the contamination from the plastic or other material not dissolved by silicon etchants on the surface of the silicon product, such as polycrystalline silicon, is a concern and needs to be quantified. Current test methods do not have adequate sensitivity for these high purity applications. For example some methods do not concentrate the plastics or use a large enough sample size. Variability in any process results in differing amounts of plastic or other surface material to be present on different pieces of silicon. Because this amount can be highly variable, testing only one or a few chunks is unlikely to give a useful test (with results ranging from very low to very high numbers). As with any statistical sampling, testing a larger amount of material reduces average variation, so it is beneficial to test a sample larger than a single piece. The test described here is flexible in that it can be used to test a significantly larger sample of silicon. This is in contrast to tests which only test a single piece or are otherwise limited in their sample size. Vessel float zoning methods do not differentiate surface carbon contamination and bulk carbon contamination. Standard Fourier Transform Infrared (FTIR) spectroscopy methods commonly used in the polysilicon industry only test the bulk carbon. Therefore, there is a need to determine the contamination from the plastic, or other material not dissolved by silicon etchants on the silicon product as no test method to quantify the amount of plastic, or other material not dissolved by silicon etchants and elementally classify the plastics, or other material not dissolved by silicon etchants on the silicon product existed prior to the method disclosed herein.

SUMMARY

A method of determining a concentration of plastic or other material not dissolved by silicon etchants contaminating a silicon product comprises: obtaining a sample of the silicon product contaminated with the plastic or other material not dissolved by silicon etchants; placing the sample of the silicon product into a ultrasonic bath liquid to produce a slurry comprising the ultrasonic bath liquid, silicon dust, and the plastic or other material not dissolved by silicon etchants; filtering the slurry with a first filter to produce a cake comprising the silicon dust and the plastic or other material not dissolved by silicon etchants separated from the sample of the silicon product; and analyzing the cake to determine the concentration of plastic or other material not dissolved by silicon etchants contaminating the silicon product.

A method of determining a concentration of plastic or other material not dissolved by silicon etchants contaminating a silicon product comprising: obtaining a sample of silicon; removing enough silicon to fill a container; immersing the silicon and the container in a ultrasonic bath liquid; agitating the sample with an ultrasonic bath; removing the container from the ultrasonic bath and removing the silicon from the container; passing the ultrasonic bath liquid from the ultrasonic bath through a first filter to remove silicon and plastic or other material not dissolved by silicon etchants from the ultrasonic bath; adding an etchant mixture to the first filter to dissolve silicon; adding additional ultrasonic bath liquid to transfer the filter contents to a second filter; vacuum drying the second filter; weighing the second filter to obtain the weight of the plastic or other material not dissolved by silicon etchants on the small filter; and calculating the amount of concentration of plastic or other material not dissolved by silicon etchants in the sample of silicon.

BRIEF DESCRIPTION OF THE DRAWINGS

The following is a brief description of the drawings wherein like elements are numbered alike and which are exemplary of the various embodiments described herein.

FIG. 1 is a graphical illustration of the test method described herein with a sample containing a higher amount of surface plastic or other non material not dissolved by silicon etchants compared to a sample containing a lower amount of surface plastic.

DETAILED DESCRIPTION

Disclosed herein is a method for determining a concentration of plastic or other material not dissolved by silicon etchants contaminating a silicon product. Quantifying the concentration of plastic or other material not dissolved by silicon etchants associated with the silicon product can be important for determining possible end uses for the silicon product.

Generally, as described herein, "the silicon product" comprises material of at least 99 percent by weight silicon. As such, the inventive method is especially useful for removing plastic or other material not dissolved by silicon etchants on the surface of the silicon product for analyzing the concentration of the plastic or other material not dissolved by silicon etchants contaminating the silicon product. However, the silicon product from which the plastic or other material not dissolved by silicon etchants can be removed by the inventive method is not limiting and can generally be used on any composition comprising at least 95 percent by weight of elemental silicon. This could include silicon from subsequent processing (such as "tops & tails"), recycled silicon, or other silicon types.

An example of the silicon product is polycrystalline silicon. Polycrystalline silicon serves as a seed material in the production of monocrystalline or multicrystalline silicon, which is used in the production of solar cells for photovoltaic cells. It can be desirable to produce monocrystalline or multicrystalline silicon with high purity, e.g., purity exceeding metallurgical grade silicon. Therefore, when the silicon product is polycrystalline silicon for producing the monocrystalline or multicrystalline silicon, it is desirable to produce polycrystalline silicon with high purity to minimize contamination contributed to the monocrystalline or multicrystalline silicon by the polycrystalline silicon. As such, the contamination of the silicon product is typically determined prior to using the silicon product as the seed material in subsequent processes.

Typically, when the silicon product is characterized as high purity, an impurity content of the silicon product is less than or equal to 1,000 parts per billion atomic (ppba). The term parts per billion atomic as used herein refers to the number of atoms of the impurity per billion atoms of the main component. In this case, the main component is silicon.

The impurity content is a measurement of the concentration of impurities contaminating the silicon product. The impurity content generally refers to the total amount of all impurities present in the silicon product unless otherwise noted. It is to be appreciated that within the class of silicon products having high purity, additional distinctions can be made based on sequentially lower impurity contents. While the above threshold for characterizing the silicon product as high purity provides an upper limit for the impurity content, the silicon product can have a substantially lower impurity content than the threshold set forth above.

Impurities, as the term is generally used herein, are defined as elements or compounds the presence of which is undesirable in the silicon product. More specific to the inventive method disclosed herein, impurities typically refer to plastic or other material not dissolved by silicon etchants. Examples of plastic or other material not dissolved by silicon etchants which the inventive method is capable of determining a concentration of can include, but are not limited to oligomers, polymers, ionomers, dendrimers, copolymers such as graft copolymers, block copolymers (e.g., star block copolymers, random copolymers, and the like), ceramics, or other materials, as well as combinations of these materials. Exemplary polymers can include, but are not limited to polyethylene, polypropylene, and fluorinated polymers.

The method of determining the concentration of plastic or other material not dissolved by silicon etchants contaminating a silicon product has many uses. For example, when establishing processing conditions for the silicon product and developing machinery for producing and handling the silicon product, it can be helpful to quantify the concentration of the plastic or other material not dissolved by silicon etchants to possibly improve the materials and methods used within the machinery. Additionally, determining the concentration of the plastic or other material not dissolved by silicon etchants contaminating the silicon product also determines possible end uses for the silicon product. Other uses of the test can include troubleshooting processes and process control. It has been discovered that current testing methods are insufficient to accurately determine the extent of the contamination from plastic or other material not dissolved by silicon etchants. However, the inventive method of determining the concentration of plastic or other material not dissolved by silicon etchants disclosed herein addresses this issue. It is to be appreciated that the physical shape of the silicon product and the physical shape of the sample is not critical to the present invention and the silicon product or sample can be in the form of rods, wafers, chunks, and particles.

The method can include obtaining a sample of the silicon product contaminated with the plastic or other material not dissolved by silicon etchants. The sample can include enough of the silicon product to be representative of the silicon product being produced. The sample can weigh about 1 to about 50,000 grams of the silicon product with the plastic or other material not dissolved by silicon etchants impurities disposed thereon. For example, the sample can weigh greater than or equal to 50 grams, for example, greater than or equal to 50,000 grams. For example, the sample can weigh about 50 to about 50,000 grams of the silicon product with the plastic or other material not dissolved by silicon etchants disposed thereon, or weight about 200 to about 20,000 grams of the silicon product with the plastic or other material not dissolved by silicon etchants disposed thereon, or weight about 1,000 to about 15,000 grams of the silicon product with the plastic or other material not dissolved by silicon etchants disposed thereon.

The form of the silicon product is not critical to the method. For example, the silicon product may be further defined as flowable recharge silicon and/or polycrystalline silicon. Common impurities of concern when working with the silicon product include plastic or other material not dissolved by silicon etchants not dissolved by etchants, for example, halogenated and non-halogenated plastic materials.

The method can also include placing the sample of the silicon product into a ultrasonic bath liquid. The ultrasonic bath liquid can comprise deionized water, organic solvents, acids, salt solutions, surfactants, and combinations comprising at least one of the foregoing. Generally, the ultrasonic bath liquid can include materials having a vapor pressure such that the material will dry if needed. However, the ultrasonic bath liquid can comprise any ultrasonic bath liquid that is non-reactive in air, i.e., has a viscosity that can allow feasible processing in other steps such as filtration. Additionally, the ultrasonic bath liquid can have a viscosity that allows for filtration of the ultrasonic bath liquid in subsequent steps.

Placing the sample in the ultrasonic bath liquid can produce a slurry comprising the ultrasonic bath liquid, silicon dust, and the plastic or material not dissolved by silicon etchants. Said differently, the ultrasonic bath liquid can separate the plastic or other material not dissolved by silicon etchants from the silicon product.

It is to be appreciated that the sample could be placed into a vessel and then the ultrasonic bath liquid can be added to the vessel already containing the sample. Alternatively, the vessel could already contain the ultrasonic bath liquid with the sample placed into the ultrasonic bath liquid. The type of vessel is not critical, but the vessel must be able to hold etchants without degrading. Additionally, the sample can be added to a container prior to placing the sample into the ultrasonic bath liquid. For example, the container can be further defined as a mesh basket. Once placed into the ultrasonic bath liquid, the mesh basket can allow the ultrasonic bath liquid to contact the sample while preventing the sample from moving freely within the ultrasonic bath liquid. The container can comprise a metal material dissolvable within the etchant liquid. For example, when the mesh basket is the container, the mesh basket comprises the metal material. Use of metal material that is dissolvable within the etchant liquid can prevent the container from introducing impurities into the etchant liquid, which would contaminate the inventive method. Examples of desirable metal materials for the container can include, but are not limited to, copper, aluminum, tin, zinc, and combinations thereof when an acid digestion method is used. Generally, in a combustion method, any metal that does not melt or contain high levels of carbon can be used. Examples of desirable metal materials for the container can include, but are not limited to, copper, aluminum, tin, silver platinum, nickel, zinc, and combinations thereof when a combustion method is used. In either etchant digestion or combustion, alloys can be used, e.g., brass and/or steel.

As introduced above, placing the sample in the ultrasonic bath liquid can produce a slurry comprising the ultrasonic bath liquid, silicon dust, and the plastic or other material not dissolved by silicon etchants. It is to be appreciated that the plastic or other material not dissolved by silicon etchants and the silicon dust can be separated from the sample by active and passive processes. For example, the sample may be placed into the ultrasonic bath liquid without any agitation of the sample within the ultrasonic bath liquid. However, it is believed that providing agitation of the sample within the ultrasonic bath liquid assists with the separation of the plastic or other material not dissolved by silicon etchants from the sample thereby ensuring a more accurate determination of the concentration of the plastic or other material not dissolved by silicon etchants contaminating the sample. For example, ultrasonic agitation can be used to assist with the separation of at least the plastic or other material not dissolved by silicon etchants from the sample. However, other methods such as megasonic agitation and etching could also be used to assist with the separation of at least the plastic or other material not dissolved by silicon etchants from the sample.

The slurry can be filtered with a first filter to produce a cake comprising the silicon dust and the plastic or other material not dissolved by silicon etchants can be separated from the sample of the silicon product. Said differently, the silicon dust and plastic or material not dissolved by silicon etchants can be separated from the ultrasonic bath liquid. Filtering the slurry can be accomplished in a variety of ways. In one embodiment, filtering the slurry can be assisted by vacuum filtration.

Once the cake is formed, the cake can be analyzed to determine the concentration of plastic or other material not dissolved by silicon etchants contaminating the silicon product. In one embodiment, analyzing the cake can be further defined as measuring an amount of carbon dioxide produced as the plastic or other material not dissolved by silicon etchants reacts with oxygen to determine the concentration of the plastic or other material not dissolved by silicon etchants contaminating the sample of the polycrystalline silicon. In such an embodiment, the cake can be placed into a total combustion instrument chamber. The chamber is enriched with oxygen and the chamber is heated. Once enriched with oxygen and heated, the plastic material reacts with the oxygen thereby releasing carbon dioxide. The amount of carbon dioxide can be measured to determine the concentration of the plastic material contaminating the sample of the polycrystalline silicon. The concentration of carbon dioxide can be monitored by a Fourier Transform Infrared Spectrometer (FTIR) or another analytical method appropriate for measuring the concentration of carbon dioxide. The amount of plastic material can be calculated based on the concentration of carbon dioxide, time, and flow rate of oxygen.

In another embodiment, analyzing the cake can include exposing the cake to an etchant liquid to dissolve the silicon dust thereby producing a residue comprising the plastic or other and the etchant liquid. The residue can then be filtered with a second filter to collect the plastic or other material not dissolved by silicon etchants. The plastic or other material not dissolved by silicon etchants retained by the second filter can then be analyzed to determine the concentration of plastic or other material not dissolved by silicon etchants contaminating the sample of the silicon product.

Analyzing the plastic or other material not dissolved by silicon etchants retained by the second filter can include comparing an initial weight of the sample of the silicon product to a weight of the plastic or other material not dissolved by silicon etchants retained by the second filter to determine the concentration of the plastic or other material not dissolved by silicon etchants contaminating the sample of the silicon product. As such, the method can include measuring the initial weight of the sample of the silicon product contaminated with the plastic or other material not dissolved by silicon etchants, and measuring the weight of the plastic or other material not dissolved by silicon etchants retained by the second filter.

It is to be appreciated that the plastic or other material not dissolved by silicon etchants retained by the second filter can be dried to eliminate any liquid to ensure an accurate measurement of the weight. As such, the plastic or other material not dissolved by silicon etchants retained by the second filter can be dried using a vacuum drier, by heating, or allowing time for the liquid to evaporate.

When employed, measuring the weight of the plastic or other material not dissolved by silicon etchants retained by the second filter can include subtracting an initial weight of the second filter from a final weight of the second filter to obtain the weight of the plastic or other material not dissolved by silicon etchants retained by the second filter. As such, the method can include measuring the initial weight of the second filter without the plastic or other material not dissolved by silicon etchants retained thereon and measuring the final weight of the second filter once the plastic or other material not dissolved by silicon etchants is retained thereon.

The method can include determining a type of plastic or other material not dissolved by silicon etchants contaminating the silicon product. As such, the method can include placing the second filter with the plastic or other material not dissolved by silicon etchants retained thereon within a second liquid to separate the plastic or other material not dissolved by silicon etchants from the second filter. The second liquid can be filtered with a third filter having an atomic mass different from the plastic or other material not dissolved by silicon etchants to retain the plastic or other material not dissolved by silicon etchants on the third filter. Generally, the third filter can comprise a material that is easily distinguished from the impurities in the tests. For example, the third filter can comprise a material having sufficient contrast to be distinguishable from the impurities during Scanning Electron Microscopy tests. For example, the third filter can be a metal filter, e.g., a silver sinter filter.

Generally, the first filter and the second filter can comprise a material that can withstand exposure to an etchant material without degrading. The first filter and the second filter can comprise a material that will allow release of the plastic or other material not dissolved by silicon etchants back into the liquid. For example, the first filter and the second filter can comprise a plastic or other material not dissolved by silicon etchants as previously described herein with respect to the impurities. The third filter does not have to release the plastic or other material not dissolved by silicon etchants back into the liquid, since passing the liquid through the third filter is one of the last steps in the test.

The third filter with the plastic or other material not dissolved by silicon etchants retained thereon can be analyzed to determine the type of plastic or other material not dissolved by silicon etchants disposed on the surface of the sample of the silicon product. It is to be appreciated that analyzing the third filter can be accomplished in a variety of ways. For example, analyzing the third filter could be performed with an energy dispersive spectrometer and/or an x-ray fluorescence spectroscopy (XRF) and/or scanning electron microscopy (SEM).

EXAMPLES

A test was conducted using the inventive method to determine the elemental composition present on a single test sample of the silicon product. The test sample was subjected to testing by energy dispersive spectroscopy (EDS) at 4-hour intervals to determine the accuracy of the final measurements. The elemental composition tested for were carbon (C), oxygen (O), fluorine (F), and chlorine (Cl). The results of the EDS test are shown in Table 1, where "Units" refers to Atomic % of the particular element measured.

TABLE 1

Elemental Composition at 4-Hour Intervals

| Element | Units @ 0 hrs | Units @ 4 hrs | Units @ 8 hrs | Units @ 12 hrs | Units @ 16 hrs |
|---|---|---|---|---|---|
| C | 28 | 26 | 39 | 30 | 34 |
| O | 21 | 25 | 16 | 18 | 18 |
| F | 51 | 49 | 45 | 52 | 48 |
| Cl | 0 | 0 | 0 | 0 | 0 |

The average value and two times the standards deviation were determined for each element tested using the EDS test. It was found that the use of the EDS test with the inventive method provided an average of two-times the standard deviation of ±8 percent at 95 percent statistical confidence.

Tests were also conducted to illustrate the effectiveness of the method disclosed herein. For example, Sample Si 1, a group of samples containing a higher level of surface impurities (e.g., surface plastic) was prepared and Sample Si 2, a group of samples containing a lower level of surface impurities was prepared. The samples were then tested according to the method disclosed herein. As demonstrated in FIG. 1, the test was able to detect the difference between the two groups of products containing different levels of surface impurities. For example, after the test, Sample Si 1 was shown to contain higher levels of surface impurities compared to Sample Si 2, where Sample Si 1 was made with a higher level of surface impurities and Sample Si 2 was made with a lower level of surface impurities. Results in FIG. 1 were measured in ppbw, with a Student's t-test between these sample sets showing that the samples are different ($P=5.7\times10^{-8}$). These results demonstrate with 95% confidence that Sample Si 1 and Sample Si 2 are different with the t-value magnitudes lower than 0.05.

As described herein the method of determining a concentration of plastic or other material not dissolved by silicon etchants contaminating a silicon product can comprise obtaining a sample of silicon (e.g., chunks, rods, etc.), and filling a container (e.g., a basket, such as a metal basket) with the silicon. The silicon and basket can then be immersed in a ultrasonic bath liquid and exposed to an ultrasonic bath which can allow the plastic or other material not dissolved by silicon etchants to be removed from the silicon into the bath. After exposure to ultrasound, the basket can be removed and the silicon removed, the basket can then be re-filled with more silicon and this process repeated until all the silicon product in the sample has been processed. The sample can be about 1 to about 50,000 grams of the silicon product with the plastic or other material not dissolved by silicon etchants disposed thereon. For example, the sample can be about 20 to about 20,000 grams of the silicon product with the plastic or material not dissolved by silicon etchants disposed thereon, or about 1,000 to about 15,000 grams of the silicon product with the plastic or other material not dissolved by silicon etchants disposed thereon.

The ultrasonic bath liquid can be run though a first filter to remove the silicon and plastic or other material not dissolved by silicon etchants from the bath. Afterward, the first filter that was used to remove the silicon and plastic or other material not dissolved by silicon etchants from the bath can be submerged in an etchant mixture to dissolve the silicon, leaving plastic. Additional liquid can be used to transfer the filter contents to a pre-weighed second filter. The pre-weighed second filter can be vacuum dried and then weighed. The earlier weight measurement can be subtracted to give the weight of the plastic or material not dissolved by silicon etchants on the filter. Dividing this answer by the starting weight of silicon in the sample gives a measurement of the concentration of plastic or other material not dissolved by silicon etchants in the sample. Optionally, additional liquid, which can be the same as or different from the liquid in the ultrasonic bath, can be used to transfer the material on the filter to a third filter, e.g., a metal filter. A scanning electron microscope can then be used at standard magnification and other settings to obtain a spectrum of the makeup of the material on the filter.

The methods disclosed herein include at least the following embodiments:

Embodiment 1

A method of determining a concentration of plastic or other material not dissolved by silicon etchants contaminating a silicon product comprising: obtaining a sample of the silicon product contaminated with the plastic or other material not dissolved by silicon etchants; placing the sample of the silicon product into a ultrasonic bath liquid to produce a slurry comprising the ultrasonic bath liquid, silicon dust, and the plastic or other material not dissolved by silicon etchants; filtering the slurry with a first filter to produce a cake comprising the silicon dust and the plastic or other material not dissolved by silicon etchants separated from the sample of the silicon product; and analyzing the cake to determine the concentration of plastic or other material not dissolved by silicon etchants contaminating the silicon product.

Embodiment 2

The method of Embodiment 1, further comprising: exposing the cake to an etchant liquid to dissolve the silicon dust thereby producing a residue comprising the plastic or other material not dissolved by silicon etchants and the etchant liquid; filtering the residue with a second filter to collect the plastic or other material not dissolved by silicon etchants; and analyzing the plastic or other material not dissolved by silicon etchants retained by the second filter to determine the concentration of plastic or other material not dissolved by silicon etchants contaminating the sample of the silicon product.

Embodiment 3

The method of Embodiment 1 or Embodiment 2, further comprising: measuring an initial weight of the sample of the silicon product contaminated with the plastic or other material not dissolved by silicon etchants; measuring a weight of the plastic or other material not dissolved by silicon etchants retained by the second filter; and comparing the initial weight of the sample of the silicon product to the weight of the plastic or other material not dissolved by silicon etchants retained by the second filter to determine the concentration of the plastic or other material not dissolved by silicon etchants contaminating the sample of the silicon product.

Embodiment 4

The method of Embodiment 3, further comprising: measuring an initial weight of the second filter without the plastic or other material not dissolved by silicon etchants retained thereon; measuring a final weight of the second filter once the plastic or other material not dissolved by silicon etchants is retained thereon; and subtracting the initial weight of the second filter from the final weight of the second filter to obtain the weight of the plastic or other material not dissolved by silicon etchants retained by the second filter.

Embodiment 5

The method of any of Embodiments 1-4, further comprising determining a type of plastic or other material not dissolved by silicon etchants contaminating the silicon product.

Embodiment 6

The method of Embodiment 5, further comprising: placing the second filter with the plastic or other material not dissolved by silicon etchants retained thereon within a liquid to separate the plastic or other material not dissolved by silicon etchants from the second filter; filtering the liquid with a third filter having an atomic mass different than the plastic or other material not dissolved by silicon etchants to retain the plastic or other material not dissolved by silicon etchants on the third filter; and analyzing the third filter with the plastic or other material not dissolved by silicon etchants retained thereon to determine the type of plastic or other material not dissolved by silicon etchants disposed on the surface of the sample of the silicon product.

Embodiment 7

The method of Embodiment 6, wherein analyzing the third filter is performed with an energy dispersive spectrometer.

Embodiment 8

The method of Embodiment 6, wherein analyzing the third filter is performed with an x-ray fluorescence spectroscopy.

Embodiment 9

The method of Embodiment 6, wherein analyzing the third filter is performed with a scanning electron microscope.

Embodiment 10

The method of Embodiment 6, wherein the third filter is further defined as a silver sinter filter.

Embodiment 11

The method of any of Embodiments 1-10, wherein analyzing the cake is further defined as: placing the cake into a total combustion instrument chamber; enriching the chamber with oxygen; heating the chamber; and measuring an amount of carbon dioxide produced as the plastic material reacts with oxygen to determine the concentration of the plastic material contaminating the sample of the polycrystalline silicon.

Embodiment 12

The method of any of Embodiments 1-11, further comprising placing the sample of the silicon product in a container prior to placing the sample of the silicon product into a ultrasonic bath liquid.

Embodiment 13

The method of Embodiment 12, wherein the container is further defined as a mesh basket comprising a metal material dissolvable within the etchant bath.

Embodiment 14

The method of Embodiment 13, wherein the metal material is selected from copper, aluminum, tin, silver, platinum, nickel, zinc, and combinations thereof.

Embodiment 15

The method of Embodiment 14, wherein the metal material is an alloy selected from brass, steel, and combinations comprising at least one of the foregoing.

Embodiment 16

The method of any of Embodiments 1-15, wherein the ultrasonic bath liquid comprises deionized water, organic solvents, acids, salt solutions, surfactants, and combinations comprising at least one of the foregoing.

Embodiment 17

The method of any of Embodiments 1-16, wherein filtering the slurry is performed by vacuum filtration.

Embodiment 18

The method of any of Embodiments 1-17, wherein the sample of the silicon product weighs 50 to 50,000 grams.

Embodiment 19

A method of determining a concentration of plastic or other material not dissolved by silicon etchants contaminating a silicon product comprising: obtaining a sample of silicon; removing enough silicon to fill a container; immersing the silicon and the container in ultrasonic bath liquid; agitating the sample with an ultrasonic bath; removing the container from the ultrasonic bath and removing the silicon from the container; passing the ultrasonic bath liquid from the ultrasonic bath through a first filter to remove silicon and plastic or other material not dissolved by silicon etchants from the ultrasonic bath; adding an etchant mixture to the first filter to dissolve silicon; adding additional liquid to transfer the filter contents to a second filter; vacuum drying the second filter; weighing the second filter to obtain the weight of the plastic or other material not dissolved by silicon etchants on the small filter; and calculating the amount of concentration of plastic or other material not dissolved by silicon etchants in the sample of silicon.

Embodiment 20

The method of Embodiment 19, wherein the liquid comprises deionized water, organic solvents, acids, salt solutions, surfactants, and combinations comprising at least one of the foregoing.

The singular forms "a," "an," and "the" include plural referents unless the context clearly dictates otherwise. "Or" means "and/or." The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group.

The suffix "(s)" is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs. A "combination" is inclusive of blends, mixtures, alloys, reaction products, and the like.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

What is claimed is:

1. A method of determining a concentration of plastic or other material not dissolved by silicon etchants contaminating a silicon product capable of testing variable amounts of silicon, including large sample sizes comprising:
   obtaining a sample of the silicon product contaminated with the plastic or other material not dissolved by silicon etchants;
   placing the sample of the silicon product into a ultrasonic bath liquid to produce a slurry comprising the ultrasonic bath liquid, silicon dust, and the plastic or other material not dissolved by silicon etchants;
   filtering the slurry with a first filter to produce a cake comprising the silicon dust and the plastic or other material not dissolved by silicon etchants separated from the sample of the silicon product;
   measuring an initial weight of the sample of the silicon product contaminated with the plastic or other material not dissolved by silicon etchants;
   exposing the cake to an etchant liquid to dissolve the silicon dust thereby producing a residue comprising the plastic or other material not dissolved by silicon etchants and the etchant liquid;
   filtering the residue with a second filter to collect the plastic or other material not dissolved by silicon etchants;
   measuring a weight of the plastic or other material not dissolved by silicon etchants retained by the second filter; and
   comparing the initial weight of the sample of the silicon product to the weight of the plastic or other material not dissolved by silicon etchants retained by the second filter to determine the concentration of the plastic or other material not dissolved by silicon etchants contaminating the sample of the silicon product.

2. The method of claim 1, further comprising:
   measuring an initial weight of the second filter without the plastic or other material not dissolved by silicon etchants retained thereon;
   measuring a final weight of the second filter once the plastic or other material not dissolved by silicon etchants is retained thereon; and
   subtracting the initial weight of the second filter from the final weight of the second filter to obtain the weight of the plastic or other material not dissolved by silicon etchants retained by the second filter.

3. The method of claim 1, further comprising determining a type of plastic or other material not dissolved by silicon etchants contaminating the silicon product.

4. The method of claim 3, further comprising:
   placing the second filter with the plastic or other material not dissolved by silicon etchants retained thereon within a liquid to separate the plastic or other material not dissolved by silicon etchants from the second filter;

filtering the liquid with a third filter having an atomic mass different than the plastic or other material not dissolved by silicon etchants to retain the plastic or other material not dissolved by silicon etchants on the third filter; and analyzing the third filter with the plastic or other material not dissolved by silicon etchants retained thereon to determine the type of plastic or other material not dissolved by silicon etchants disposed on the surface of the sample of the silicon product.

5. The method of claim 4, wherein analyzing the third filter is performed with an energy dispersive spectrometer.

6. The method of claim 4, wherein analyzing the third filter is performed with an x-ray fluorescence spectroscopy.

7. The method of claim 4, wherein analyzing the third filter is performed with a scanning electron microscope.

8. The method of claim 4, wherein the third filter is further defined as a silver sinter filter.

9. The method of claim 1, wherein analyzing the cake is further defined as:

placing the cake into a total combustion instrument chamber;

enriching the chamber with oxygen;

heating the chamber; and measuring an amount of carbon dioxide produced as the plastic or other material not dissolved by silicon etchants reacts with oxygen to determine the concentration of the plastic or other material not dissolved by silicon etchants contaminating the sample of the polycrystalline silicon.

10. The method of claim 1, further comprising placing the sample of the silicon product in a container prior to placing the sample of the silicon product into a ultrasonic bath liquid.

11. The method of claim 10, wherein the container is further defined as a mesh basket comprising a metal material dissolvable within the etchant bath.

12. The method of claim 11, wherein the metal material is selected from copper, aluminum, tin, silver, platinum, nickel, zinc, and combinations thereof.

13. The method of claim 12, wherein the metal material is an alloy selected from brass, steel, and combinations comprising at least one of the foregoing.

14. The method of claim 1, wherein the ultrasonic bath liquid comprises deionized water, organic solvents, acids, salt solutions, surfactants, and combinations comprising at least one of the foregoing.

15. The method of claim 1, wherein filtering the slurry is performed by vacuum filtration.

16. The method of claim 1, wherein the sample of the silicon product weighs 50 to 50,000 grams.

17. A method of determining a concentration of plastic or other material not dissolved by silicon etchants contaminating a silicon product comprising:

opening a sample of silicon;

removing enough silicon to fill a container;

immersing the silicon and the container in a ultrasonic bath liquid;

agitating the sample with an ultrasonic bath;

removing the container from the ultrasonic bath and removing the silicon from the container;

passing the ultrasonic bath liquid from the ultrasonic bath through a first filter to remove silicon and plastic or other material not dissolved by silicon etchants dust from the ultrasonic bath;

adding an etchant mixture to the first filter to dissolve silicon;

adding additional liquid to transfer the filter contents to a second filter;

vacuum drying the second filter;

weighing the second filter to obtain the weight of the plastic or other material not dissolved by silicon etchants on the second filter;

measuring a final weight of the second filter once the plastic or other material not dissolved by silicon etchants is retained thereon; and calculating the amount of concentration of plastic or other material not dissolved by silicon etchants in the sample of silicon by subtracting an initial weight of the second filter from the final weight of the second filter to obtain the weight of the plastic or other material not dissolved by silicon etchants retained by the second filter.

18. The method of claim 17, wherein the liquid comprises deionized water, organic solvents, acids, salt solutions, surfactants, and combinations comprising at least one of the foregoing.

* * * * *